United States Patent [19]
Hochfeld

[11] Patent Number: 5,551,612
[45] Date of Patent: Sep. 3, 1996

[54] STICK-ON CONDOM PACKAGE ASSEMBLY

[75] Inventor: Stanley Hochfeld, Howard Beach, N.Y.

[73] Assignee: Leonard Holtz, New York, N.Y.; a part interest

[21] Appl. No.: 187,758

[22] Filed: Jan. 27, 1994

[51] Int. Cl.⁶ .......................... B65D 57/00; B65D 65/10; B65D 65/14
[52] U.S. Cl. ..................... 224/219; 224/101; 224/901; 206/69; 128/844
[58] Field of Search ..................... 224/101, 901, 224/219; 40/315, 1.6; 63/20; 206/69, 38; 128/844

[56] References Cited

U.S. PATENT DOCUMENTS

| | | | |
|---|---|---|---|
| 2,006,212 | 6/1935 | Grabler | 220/608 |
| 3,651,818 | 3/1972 | Vargo | 224/901 |
| 3,677,225 | 7/1972 | Czirely. | |
| 4,638,790 | 1/1987 | Conway et al. | 128/844 |
| 4,738,357 | 4/1988 | Martin et al. | 206/69 |
| 4,741,434 | 5/1988 | Liebman. | |
| 4,844,394 | 7/1989 | Randolph. | |
| 4,875,491 | 10/1989 | Parrone | 224/901 |
| 4,942,071 | 7/1990 | Frye. | |
| 5,117,841 | 6/1992 | McBeth. | |
| 5,158,556 | 10/1992 | Stanley. | |
| 5,172,430 | 12/1992 | Lerma-Solis. | |
| 5,183,460 | 2/1993 | Scherz | 128/844 |
| 5,332,087 | 7/1994 | McMahon | 206/69 |

OTHER PUBLICATIONS

3M Medical Specialties Tape Products; 3M HealthCare, St. Paul, Minnesota, 1992.

Primary Examiner—Henry J. Recla
Assistant Examiner—Charles R. Eloshway
Attorney, Agent, or Firm—Frishauf, Holtz, Goodman, Langer & Chick

[57] ABSTRACT

A stick-on flexible condom package which contains a condom sealed therein has a rear surface on which adhesive is applied. The adhesive is contacted with a skin portion of a user for adhering the condom package to a skin portion of the user to maintain the condom package readily available for use. The adhesive may be a layer applied to a rear surface of the condom package, or may be a double-sided (double coated) adhesive member applied to the rear surface of the condom package. The double-sided adhesive member may have a foam central layer which is resilient and flexible, to improve conformability of the condom package to surface contours of the body of a user.

8 Claims, 2 Drawing Sheets

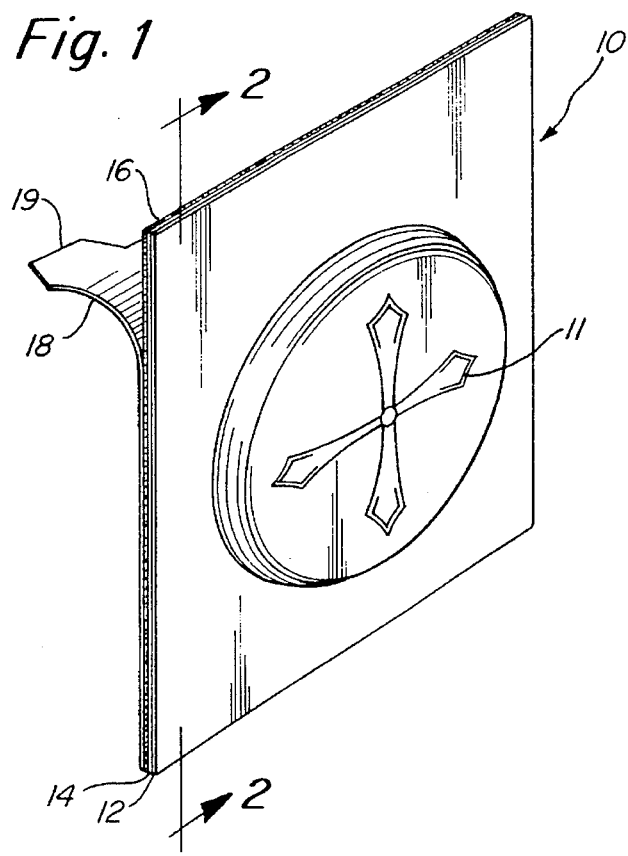
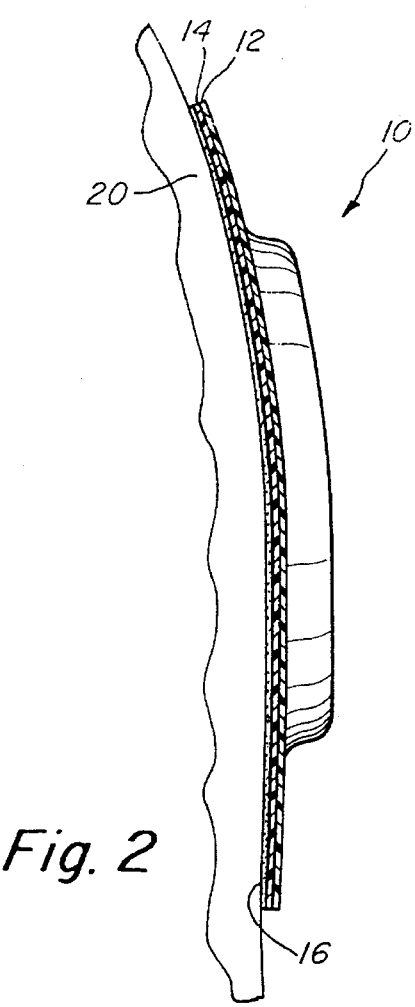
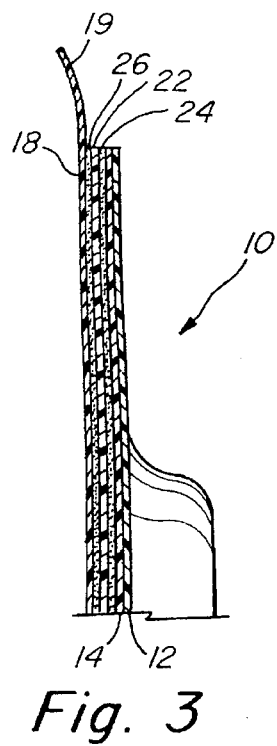
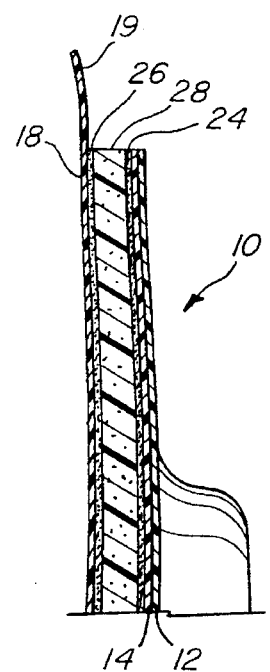
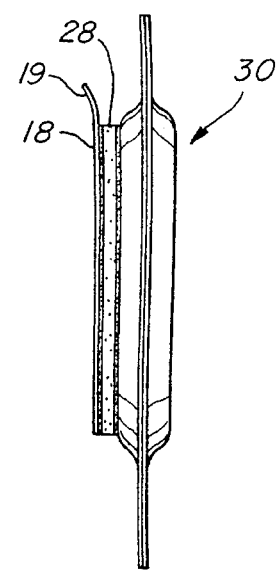
Fig. 1
Fig. 2
Fig. 3
Fig. 4
Fig. 5

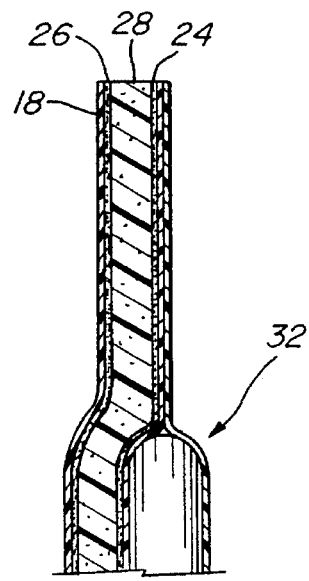
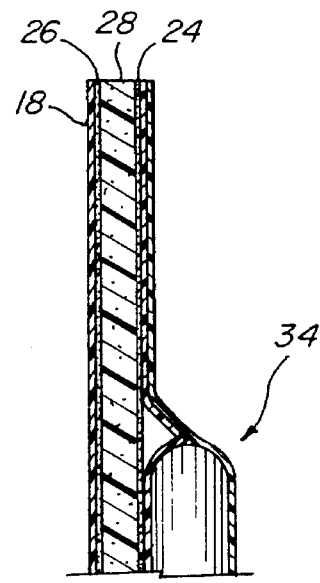
*Fig. 6*  *Fig. 7*
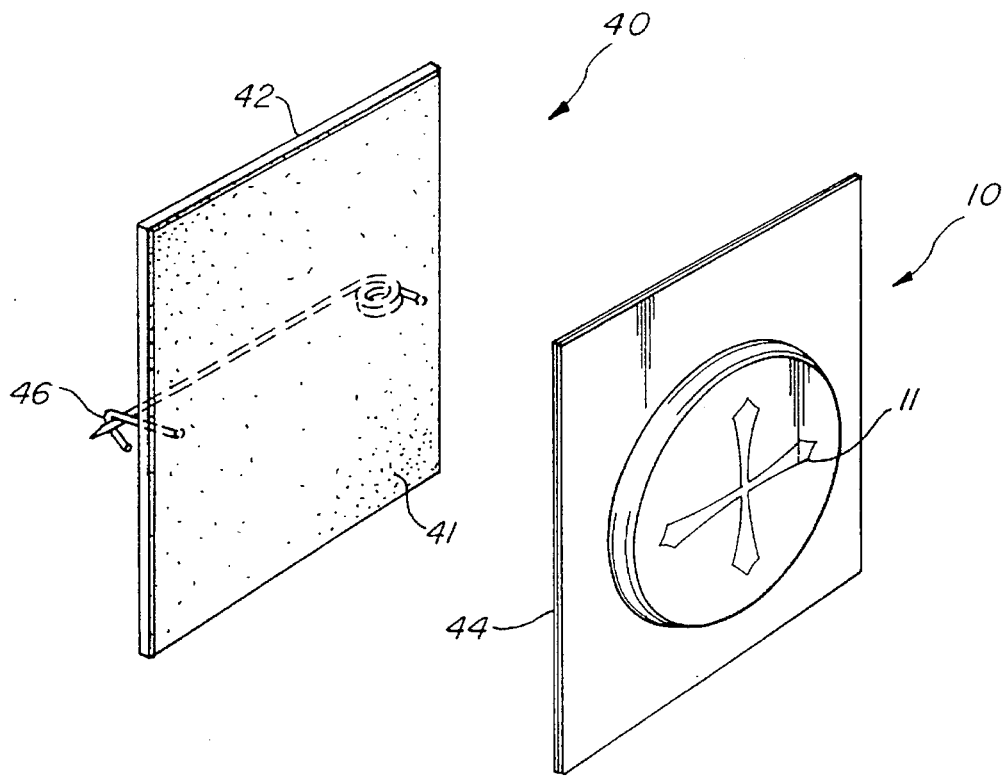
*Fig. 8*

5,551,612

STICK-ON CONDOM PACKAGE ASSEMBLY

BACKGROUND OF THE INVENTION

This invention relates to condom packages, and more particularly to a stick-on condom package which can be adhered to the skin of a potential user, or which can be otherwise attached to a user, and which can thus always be kept in a ready-to-use condition.

At the present time, there is much publicity and advertising concerning the use of condoms for health purposes as well as for birth control purposes, and particularly to curb the spreading of diseases, such as AIDS. Additionally, government sponsored advertising campaigns have been instituted in the United States and throughout the world to promote the use of condoms.

A problem currently existing is that the condoms are often not readily available precisely at the time they should be used. This is especially the case in the event of rape.

The object of the present invention is to provide a readily available condom, which is always conveniently available for immediate use.

A further object of the invention is to provide such a readily available condom in a package which is not only easy to access, but which is also adapted to be adhered to the body of a user, in a convenient and comfortable position so that it is conveniently always available for immediate use.

Still another object of the invention is to provide such a readily available stick-on condom package which, once adhered to the body, can be easily removed, but which will not be washed off, for example, in a shower or bath, and which will not come off the body when subjected to perspiration or other moisture.

Still another object of the invention is to provide a stick-on condom package which can be removably stuck onto the body of a user, and which has decorative matter thereon. The decorative matter can be imprinted or applied to an outer surface of the condom packaging.

Yet another object of the invention is to provide a stick-on condom package which is readily observable so that the user makes potential partners aware that a condom is available for use and will be used.

SUMMARY OF THE INVENTION

According to the present invention, a stick-on condom package assembly comprises a condom package containing a condom sealed therein, the condom package having a rear surface; and adhesive means on the rear surface of the condom package for adhering the condom package to a skin portion of a user. Preferably, a peel-off release layer covers the adhesive means on the rear surface of the condom package for protecting the adhesive means prior to use thereof.

The adhesive means preferably comprises a double-sided (double coated) adhesive member having a flexible central substrate, a first adhesive layer on one surface of the central substrate and adhered to the rear surface of the condom package, and a second adhesive layer on the other surface of the central substrate and which is covered by a peel-off release layer. The second adhesive layer is adapted to be secured to a skin portion of the user after removal of the peel-off release layer. The double-sided adhesive member may comprise a central thin film flexible substrate on which said first and second adhesive layers are applied, or a central resilient and flexible foam layer having a predetermined thickness and having said first and second adhesive layers applied on opposite surfaces thereof. The foam layer improves conformability of the condom package to surface contours of the body of the user.

According to another aspect of the present invention, a method of using a condom comprises providing a condom package containing a condom sealed therein, the condom package having a rear surface, and adhesive means on the rear surface of the condom package; and adhering the adhesive means on the rear surface of the condom package to a skin portion of a user for maintaining the condom package readily available for use. When ready for use, the adhesively secured condom package is peeled off from the skin portion of a user, and the condom is removed from the package and applied to a body part for use.

Preferably, the condom package has a peel-off release layer covering the adhesive means on the rear surface of the condom package for protecting the adhesive means prior to use, and the release layer is peeled off prior to applying the adhesive means to the skin portion of the user.

BRIEF DESCRIPTION OF THE DRAWINGS

FIG. 1 is a perspective view showing a condom package assembly according to the present invention;

FIG. 2 is a sectional view thereof along the line II—II in FIG. 1, with the condom package applied to the skin of a person;

FIG. 3 is a fragmentary cross sectional view of an alternative embodiment showing attachment of an adhesive in the form of a double coated adhesive sheet or tape to the back of a condom package;

FIG. 4 is a fragmentary cross sectional view of another alternative embodiment wherein a foam interlayer is provided for resiliency, thereby enhancing comfort and enabling the condom package to better conform to the body of a user;

FIG. 5 is a side view of a modified embodiment of the invention;

FIG. 6 is a fragmentary cross sectional view of another embodiment of the invention;

FIG. 7 is a fragmentary cross sectional view of still another embodiment of the invention; and FIG. 8 illustrates another embodiment of the invention.

DETAILED DESCRIPTION

Referring to FIGS. 1 and 2, a condom package assembly according to the present invention comprises a conventional-type condom package 10 which generally comprises two layers 12, 14 which are, for example, made of metal foil or thin plastic sheets which are sealed together to form a sealed air tight condom package, in a conventional manner. Alternatively, the layers 12, 14 can be formed of any other conventional materials which are conventionally used for packaging condoms. The condom package 10 may be any form or shape presently used in condom packaging, or may take any desired shape. The packaging is preferably provided with a substantially flat back layer 14 to which an adhesive layer 16 is applied, as shown in FIGS. 1 and 2. The adhesive layer 16 can be either sprayed on or applied as a liquid or the like, or can be applied as an adhesive coating in any other conventional manner. The adhesive layer 16 can also be a film-type adhesive layer which is pressed on or otherwise adhered to back surface 14 of the condom package. The adhesive layer 16, after being applied to the backing of the package 10 has a peel-off release layer 18 placed thereon to protect the adhesive during transit and/or handling prior to use. The release layer 18 has an extended pull tab portion 19 to facilitate removal thereof. The condom package 10 is preferably flexible so that it can be bent, for example, as shown in FIG. 2, to conform to the surface of the skin of a person.

FIG. 2 shows the stick-on condom package 10 of the present invention applied to the skin 20 of a person. The skin 20 is a curved body portion and the adhesive layer 16 is removably adhered thereto after first peeling off the release layer 18.

The adhesive layer 16 is of such a nature as to be easily removable from the body, preferably without pain to the person using the device. Moreover, the adhesive layer 16 is preferably of a waterproof or water resistent adhesive so that once applied to the body of the person, it will not fall off or inadvertently be removed due to perspiration of the body and/or due to exposure to water, such as a shower, bath or swimming. Typical adhesives suitable for use as adhesive layer 16 are medical adhesive tapes which are available from 3M Corporation, some of which are identified hereinbelow.

The release layer 18 may be paper or plastic coated paper or a plastic sheet, or any other conventional release layer used for similar purposes.

As shown in FIG. 1, the outer surface of the condom package 10 may have a decorative design 11 thereon so that when the condom package is mounted to an exposed body portion of the wearer, it also serves as a decorative article. The decoration in FIG. 1 is shown as being printed or otherwise applied thereon. Alternatively, the decoration may be adhered (i.e., by an adhesive) to the outer surface of the condom package and may also take the form of jewelry or any other decorative object secured or attached to the outer viewable surface of the condom. The design 11 of FIG. 1 is only an example. Any decorative or other pictorial or text design (even advertising) can be used, as desired.

FIG. 3 shows an alternative embodiment wherein the adhesive layer 16 of the embodiment of FIGS. 1 and 2 is replaced by an adhesive member such as a double-sided (double coated) adhesive tape or sheet having opposed adhesive surfaces and a central substrate (preferably flexible). More particularly, as shown in FIG. 3, the adhesive-tape member comprises a central flexible substrate 22 having an adhesive layer 24, 26 on opposite sides thereof. The adhesive member (hereinafter generally referred to as double coated adhesive tape) is applied to the back surface of the rear layer 14 of the condom package 10. The outer adhesive surface 26 has a release layer or peel paper 18 thereon to protect the adhesive layer 26. The condom package is made ready for sticking to the skin of a person's body by peeling off of the release layer or peel paper 18 (via the pull tab 19) from the back surface of the condom package assembly, to expose the adhesive layer 26. The package 10 is then adhered to the skin of a person, as shown in FIG. 2.

Preferably, a double coated medical tape is useful as the double coated adhesive member of FIG. 3. A double coated medical tape which is particularly suitable is tape number 1509 or 1512 manufactured by 3M Health Care, St. Paul, Minnesota. These double coated medical tapes have a central flexible substrate 22 made of a polyethylene film with adhesive material 4, 26 coated on both opposite sides thereof. Tapes 1509 and 1512 are particularly suitable since they are made to be adhered to the skin of a human being, provide a fluid barrier (waterproof), are conformable, are easily removable from the skin, and are hypoalergenic. All of these characteristics are particularly important in the present invention.

FIG. 4 illustrates a further modified embodiment wherein the double-sided (double coated) adhesive tape member 22, 24, 26 of FIG. 3 is replaced by a double-sided foam-type adhesive tape member. The central foam layer 28 replaces the thin flexible central substrate layer 22 of the embodiment of FIG. 3, and is provided so that the resultant structure more closely conforms to curves and other irregularities in the body (skin) surface of the user and improves adherence and retention of the condom package to the body of the user. In other respects, the embodiment of FIG. 4 is similar to that of FIG. 3.

A particularly suitable double sided or double coated foam tape is tape number 1511 manufactured by 3M Health Care, St. Paul, Minn. This product has a central foam layer of polyvinyl chloride foam which is approximately 0.9 mm thick, with adhesive coated on both opposite sides thereof. Tape number 1511 from 3M Health Care has similar characteristics as the two tapes referred to above (tapes 1509 and 1512), thereby making it particularly suitable for application to the present invention. Other thicknesses of the foam central layer 28 can be used, as desired. For example, a thickness of anywhere up to about 0.2 mm or even greater can be used. Polyvinyl chloride foam is used in tape number 1511, but other suitable resilient foam materials could be used as desired.

In some instances, the rear surface of the condom package may not be flat as shown in FIGS. 1–4. In such instances, such as shown in FIG. 5, the rear surface of the condom package 30 may be bulged outwardly. In such cases, it is preferable to use a double sided foam core adhesive tape member such as shown in FIG. 4. In this arrangement, the foam will serve as a structural support for the adhesive material and will provide better sticking of the condom package 30 onto the skin of a user However, even in this embodiment of FIG. 5 the conventional double sided tape shown in FIG. 3 could be used, but retention will probably be somewhat higher when using the foam core tape of FIG. 4.

FIGS. 6 and 7 show modified embodiments using condom packages 32, 34, respectively, which are similar to the condom package 30 of FIG. 5. Foam core double coated tapes or sheets (like that in FIG. 4) are used in the embodiments of FIGS. 6 and 7. In FIG. 6, the foam core double coated tape or sheet 24, 26, 28 is deformed to conform with the shape of the rear of the condom package 32. In FIG. 7, the foam core double coated tape or sheet remains substantially flat and the condom package 34 is deformed (flattened) to adhere to the flat adhesive member.

In the embodiments of FIGS. 1–4, 6 and 7, the adhesive covers the entirety of the rear surface of the condom package. As should be readily apparent the adhesive may only partly cover the rear surface portion of a condom package, so long as sufficient adhesive surfaces are provided to enable secure retention on the body of a person.

The stick-on condom package can be stuck onto any desired body part, for example on the torso (including stomach or chest area), groin area, shoulder, back, etc., as desired. When the package has a design on the outer surface thereof, the package may be worn on (stuck onto) an exposed body part such as a shoulder, arm, leg, etc., or may be stuck onto the outer surface of an article of clothing, as desired.

FIG. 8 illustrates yet another embodiment of the invention wherein a backing member 40 with a spring pin 46 or other attachment means is provided for removably attaching the condom package to an article of clothing of a wearer. The adhesive layer 41 can either be applied to the support layer 42 of backing member 40, or it can be applied to the rear surface 44 of the condom package 10. The pin 46 is a conventional type of pin used in costume jewelry or the like. The condom package 10 may have a decorative outer surface with a design 11 thereon, or may have an article of jewelry or other decorative object mounted thereon.

The article of FIG. 8 can be secured by means of the pin 46 or other attachment means to the outside of an article of clothing of a user, wherein it will be readily observed or it can be removably attached to an inner surface of clothing wherein it is hidden. The attachment means of FIG. 8 can also be used with the condom packages of FIGS. 5–7, or with any other type of condom package.

While the invention has been described above with respect to specific embodiments and structures, various modifications and alterations can be made and various features of the different embodiments can be combined, in any operable combination, within the scope of the invention, as defined in the appended claims.

What is claimed is:

1. A stick-on condom package assembly, comprising:

a completely sealed condom package containing a condom completely sealed therein, said completely sealed condom package being flexible and having a rear wall connected to a front wall, to completely enclose said condom within said flexible package in an original, sealed non-use condition;

an adhesive layer means on the rear wall of said completely sealed condom package for adhering said completely sealed condom package, in its originally sealed condition, to a skin portion of a user; and a peel-off release layer covering said adhesive layer means on the rear wall of said condom package for covering and protecting said adhesive layer means prior to use thereof, said adhesive layer means being adapted to be removably secured to a skin portion of the user after removal of said peel-off release layer, and said adhesive layer means being easily removable from the skin portion of the user when the user is ready to use the condom in said flexible package, and said front wall being permanently and non-detachably adhered to said rear wall and being free of any opening means such that said flexible package is openable only after removal thereof from the skin portion of the user when it is ready for use.

2. The stick-on condom package assembly of claim 1, wherein said adhesive layer means comprises a double-sided adhesive member having a central substrate, a first adhesive layer on one surface of said central substrate and adhered to the rear wall of said condom package, and a second adhesive layer on the other surface of said central substrate and covered by a protective peel-off release layer, said second adhesive layer being adapted to be secured to a skin portion of the user after removal of said peel-off release layer.

3. The stick-on condom package assembly of claim 2, wherein said central substrate on which said first and second adhesive layers are applied comprises a flexible thin film substrate.

4. The stick-on condom package assembly of claim 2, wherein said central substrate comprises a resilient and flexible foam layer having a predetermined thickness and having said first and second adhesive layers on opposite surfaces thereof, for improving conformability of the flexible condom package to surface contours of the body of the user.

5. The stick-on condom package assembly of claim 2, wherein said rear wall of said condom package is substantially flat.

6. The stick-on condom package assembly of claim 2, wherein said rear wall of said flexible condom package is bulged outwardly, and wherein said flexible foam layer serves as a support means for said second adhesive layer opposite said bulged out portions of said flexible condom package.

7. The stick-on condom package assembly of claim 1, wherein said rear wall of said condom package is substantially flat.

8. A method of using a condom, comprising:

providing a completely sealed condom package containing a condom completely sealed therein, said completely sealed condom package being flexible and having a rear wall connected to a front wall to completely enclose said condom within said package in an original, sealed, non-use condition, said front wall being permanently and non detachably adhered to said rear wall and being free of any opening means, said completely sealed condom package further having an adhesive layer on the rear wall of said condom package and a peel-off release layer covering said adhesive layer for protecting said adhesive layer prior to use;

peeling off said peel-off release layer prior to applying said adhesive layer to a skin portion of the user;

thereafter adhering said adhesive layer on the rear wall of said completely sealed condom package to the skin portion of a user for maintaining said condom package readily available for use;

thereafter peeling said completely sealed condom package, in its original, sealed, non-use condition, from the skin portion of a user: and thereafter opening said completely sealed condom package, then removing the condom from the opened package, and then applying said condom to a body part for use.

\* \* \* \* \*